United States Patent
Xu et al.

(10) Patent No.: US 10,071,032 B2
(45) Date of Patent: Sep. 11, 2018

(54) HIGH SALT TOOTHPASTE AND METHODS FOR USING SAME

(71) Applicant: Colgate-Palmolive Company, New York, NY (US)

(72) Inventors: Yun Xu, Langhorne, PA (US); Dorathy Zeng, Guangzhou (CN); Kahn Tan, Guangzhou (CN); Pingdong Li, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 7 days.

(21) Appl. No.: 15/529,243

(22) PCT Filed: Dec. 15, 2014

(86) PCT No.: PCT/CN2014/093826
§ 371 (c)(1),
(2) Date: May 24, 2017

(87) PCT Pub. No.: WO2016/095083
PCT Pub. Date: Jun. 23, 2016

(65) Prior Publication Data
US 2017/0319449 A1    Nov. 9, 2017

(51) Int. Cl.
| | | |
|---|---|---|
| *A61K 8/21* | (2006.01) | |
| *A61K 8/27* | (2006.01) | |
| *A61Q 11/00* | (2006.01) | |
| *A61K 8/19* | (2006.01) | |
| *A61K 8/20* | (2006.01) | |
| *A61K 8/24* | (2006.01) | |
| *A61K 8/25* | (2006.01) | |
| *A61K 8/365* | (2006.01) | |
| *A61K 8/60* | (2006.01) | |
| *A61K 8/86* | (2006.01) | |

(52) U.S. Cl.
CPC ............... *A61K 8/27* (2013.01); *A61K 8/19* (2013.01); *A61K 8/20* (2013.01); *A61K 8/24* (2013.01); *A61K 8/25* (2013.01); *A61K 8/365* (2013.01); *A61K 8/60* (2013.01); *A61K 8/86* (2013.01); *A61Q 11/00* (2013.01); *A61K 2800/48* (2013.01)

(58) Field of Classification Search
None
See application file for complete search history.

(56) References Cited

U.S. PATENT DOCUMENTS

| | | |
|---|---|---|
| 4,656,031 A | 4/1987 | Lane et al. |
| 5,624,906 A * | 4/1997 | Vermeer ............... A61K 8/60 514/23 |
| 8,491,873 B2 | 7/2013 | Murakami |
| 2007/0059256 A1 | 3/2007 | Kato |
| 2015/0297500 A1 | 10/2015 | Robinson et al. |

FOREIGN PATENT DOCUMENTS

| | | |
|---|---|---|
| CN | 1192897 A | 9/1998 |
| EP | 1203574 | 5/2002 |
| JP | 2009-263271 | 11/2009 |
| WO | WO 2006/012967 | 2/2006 |
| WO | WO 2010/121619 | 10/2010 |

OTHER PUBLICATIONS

International Search Report and Written Opinion in International Application No. PCT/CN2014/093826, dated Sep. 1, 2015.
Mori, 1988, "Tooth paste composition containing sodium chloride—and anionic surfactant, to which dextrin is compounded," Database WPI, Week 198815, Thomson Scientific AN 1988-103049 & JP S63 54314 A(Sunstar KK).

* cited by examiner

*Primary Examiner* — Nannette Holloman

(57) ABSTRACT

Compositions and methods of treating and/or preventing conditions of the oral cavity, e.g. gingivitis, comprise applying a toothpaste composition comprising at least 5% sodium chloride in a toothpaste base comprising a zinc salt, non-silica calcium carbonate abrasive and humectant, to the oral surfaces, e.g., the teeth and gums, of a patient in need thereof.

15 Claims, No Drawings

HIGH SALT TOOTHPASTE AND METHODS FOR USING SAME

FIELD

The present invention relates to toothpaste compositions that contain high levels of sodium chloride in a calcium carbonate base, and a source of zinc. The present invention also provides methods for treating conditions of the oral cavity, e.g., gingivitis.

BACKGROUND

Gum disease affects a significant number of people worldwide, and is a leading cause of tooth loss. Gum disease usually begins with gingivitis, in which bacteria in dental plaque build up, causing the gums to become inflamed. Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. A wide variety of antibacterial agents have been suggested in the art to retard plaque formation. For example, halogenated hydroxydiphenyl ether compounds such as triclosan are well known to the art for their antibacterial activity and have been used in oral compositions to counter plaque formation by bacterial accumulation in the oral cavity. However, many people prefer to use natural products to provide antibacterial activity. Accordingly, there exists a need for methods of treating gingivitis using natural products having antibacterial activity.

Zinc is a well-known antimicrobial agent used in toothpaste compositions. At effective concentrations, zinc has been shown to inhibit bacterial glycolysis and the activity of bacterial proteases. Zinc is also a well-known essential mineral for human health, and has been reported to help strengthen dental enamel and to promote cell repair. Unfortunately, conventional toothpaste formulations often require high concentrations of zinc, e.g., 2% by weight or more, to achieve efficacy. At this concentration, the zinc imparts a notably astringent taste to the composition. There is thus a need for improved antibacterial toothpaste formulations that do not suffer from the drawbacks of conventional compositions.

SUMMARY

Unless otherwise indicated, the terms "%" or "percent", when used in connection with toothpaste compositions described herein, are intended to refer to the percent by weight of the indicated ingredient in the toothpaste composition.

In some embodiments, the present invention provides a method of treating and/or preventing diseases or conditions of the oral cavity, e.g. gingivitis or halitosis, comprising contacting the oral surfaces, e.g., the teeth and gums, of a patient in need thereof with a toothpaste composition containing at least 5% sodium chloride by weight of the toothpaste composition in a toothpaste base comprising calcium carbonate and humectant. In some further embodiments, the toothpaste for use in the method contains from 5% to 15% sodium chloride, for example from 8% to 12% sodium chloride. In some embodiments, the toothpaste contains about 10% sodium chloride.

In some embodiments, the toothpaste comprises natural calcium carbonate, in an amount of from 10% to 45% by weight of the toothpaste composition, or from 25% to 40%, or from 30% to 35%; or about 32%.

In some embodiments, the toothpaste further comprises a zinc salt, e.g., zinc citrate. For example, in a natural calcium carbonate based composition that comprises 5% to 15% sodium chloride, the toothpaste may include a zinc salt, e.g. zinc citrate, in an amount of from about 0.1 to 1%, e.g., 0.1 to 0.5%, or e.g., 0.2%.

In further embodiments, the invention provides a toothpaste comprising (a) natural calcium carbonate, (b) sodium chloride, and (c) an effective antimicrobial amount of a zinc salt. In some further embodiments, the natural calcium carbonate is present in an amount of from 10% to 45% by weight of the toothpaste composition, or from 25% to 40%, or from 30% to 35%; or about 32%. In some further embodiments, the sodium chloride is present in an amount from 5% to 15%, for example from 8% to 12% sodium chloride, e.g., about 10%. In some further embodiments, the antimicrobial zinc salt is present in an amount of 0.1 to 1%, e.g., 0.1 to 0.5%, or e.g., 0.2%. In some further embodiments, the zinc salt is zinc citrate.

In further embodiments, the toothpaste of any of the preceding embodiments further includes one or more humectants. In some embodiments, the humectant is sorbitol, which is present in an amount of from 16% to 26% by weight of the toothpaste composition; or from 18% to 24%; or about 21%.

In some embodiments, the toothpaste of any of the preceding embodiments further includes one or more detergents or surfactants. In some embodiments, the toothpaste further includes sodium lauryl sulfate and a poloxamer, for example and without limitation poloxamer 407. In some embodiments, the sodium lauryl sulfate is present in an amount of from 1% to 3% by weight of the toothpaste composition, for example about 2%, and poloxamer 407 is present in an amount of from 0.5% to 2%, for example about 1%.

In some embodiments, the toothpaste of any of the preceding embodiments further includes one or more binding agents. In some embodiments, the binding agent includes or consists of a carboxymethylcellulose, for example and without limitation CMC 2000s, in an amount of from 0.5% to 1.2% by weight of the toothpaste composition; or from 0.7% to 1%; or for example 0.8% to 0.9%.

In some embodiments, the toothpaste of any of the preceding embodiments further includes a fluoride source, for example and without limitation monofluorophosphate (MFP), sodium fluoride, or stannous fluoride. In some embodiments, the fluoride source is MFP, which is present in an amount of from 0.5% to 1% by weight of the toothpaste composition; or 0.6% to 0.9%, for example 0.7% to 0.8%.

In some embodiments, the toothpaste of any of the preceding embodiments further includes a thickener, for example and not limitation thickener silica, for example in an amount of from 1% to 3% by weight of the toothpaste composition, for example about 2%.

In some embodiments, the toothpaste of any of the preceding embodiments further includes one or more adjuvants selected from sweetening agents, flavoring agents and coloring agents. In some embodiments, the toothpaste contains flavoring in an amount of from 0.5% to 3.0% by weight of the toothpaste composition; 0.8% to 1.6%; or about 1.2%.

In some embodiments, the toothpaste of any of the preceding embodiments includes from 5% to 15% sodium chloride, for example from 8% to 12% sodium chloride, from 30% to 35% calcium carbonate; from 16% to 26% sorbitol; from 1% to 3% SLS, and from 0.5% to 2% poloxamer 407. In some such embodiments, the toothpaste further includes from 0.5% to 1.0% MFP; and from 0.5% to 1.2% CMC 2000s. In some further such embodiments, the toothpaste further includes a thickener, for example thickener silica, for example in an amount of from 1% to 3%, and flavoring, for example in an amount of from 0.5% to 2.0%.

In some embodiments, the toothpaste of any of the preceding embodiments includes about 32% calcium carbonate; about 21% sorbitol; about 10% sodium chloride; about 2% thickener silica; about 2% sodium lauryl sulfate; about 1% poloxamer 407; 0.8%-0.9% CMC2000s; and 0.7%-0.8% monofluorophosphate.

DETAILED DESCRIPTION

It has been discovered in accordance with the present invention that high levels of the natural ingredient sodium chloride can function in toothpaste for use in treating gingivitis, as an effective antibacterial agent. The antibacterial activity provides significant benefits by preventing or retarding bacterial growth both in the toothpaste during storage, and in use. In some embodiments, the invention provides toothpaste for use in treating and/or preventing conditions of the oral cavity, e.g. gingivitis, having such high levels of sodium chloride formulated with a sorbitol-based humectant system, together with a calcium carbonate abrasive.

The present invention provides toothpastes for use in treating and/or preventing conditions of the oral cavity, e.g. gingivitis or halitosis, that contain at least about 5% sodium chloride, together with abrasive and humectant. In some embodiments, the toothpastes contain from 5% to 15% sodium chloride, by weight of the toothpaste, for example 8% to 12% sodium chloride. In some embodiments, the toothpaste contains about 10% sodium chloride. While not wishing to be bound by any theory, the inclusion of high levels of sodium chloride in accordance with the invention is believed to impart antibacterial properties to the compositions, providing benefits in terms of both minimizing bacterial growth during storage and antibacterial efficacy during use.

The present invention further provides toothpaste compositions as described above, further comprising a zinc salt, e.g., zinc citrate. The inventors have unexpectedly found that zinc is an effective antimicrobial booster in high salt, natural calcium carbonate-based toothpaste compositions at a concentration much lower than that which is effective in traditional silica-based toothpaste compositions. For example, in a natural calcium carbonate based composition that comprises 5% to 15% sodium chloride, zinc citrate is effective in an amount of from about 0.1 to 1%, e.g., 0.1 to 0.5%, or e.g., 0.2%. In contrast, conventional zinc containing toothpaste compositions typically employ zinc salts at concentrations of 1% to 2% or higher, resulting in an unfavorable astringent taste.

The toothpastes of any of the preceding embodiments further comprise an abrasive, e.g. selected from abrasive silica and/or calcium salts, e.g. calcium carbonate and/or a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate. In a particular embodiment, the abrasive includes or is composed of calcium carbonate. Any of the calcium carbonates known to be useful in the dentifrice art are suitable for inclusion in the toothpastes of the present invention. In some embodiments, the calcium carbonate is natural calcium carbonate (NCC), preferably in a particle size or distribution of particle sizes wherein 99.5% or greater of the particles passes through a 325 mesh (44 micron). The amount of calcium carbonate in the toothpastes for use in treating gingivitis is for example from 10% to 60%, e.g. 10% to 45%. In some embodiments, the amount of calcium carbonate in the toothpastes for use in treating gingivitis is from 25% to 40%, or from 30% to 35%. In some embodiments calcium carbonate is present in an amount of about 32%.

The toothpastes of any of the preceding embodiments may also contain a fluoride source—i.e., a fluoride-containing compound having a beneficial effect on the care and hygiene of the oral cavity, e.g. diminution of enamel solubility in acid and protection of the teeth against decay. Examples of suitable fluoride sources include sodium fluoride, stannous fluoride, potassium fluoride, potassium stannous fluoride (SNFZ-KF), potassium fluorozirconate, sodium hexafluorostannate, stannous chlorfluoride, and sodium monofluorophosphate (MFP). Where present, the fluoride source would provide fluoride ion in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. The amount by weight of these materials, which dissociate or release fluoride or fluorine-containing ions, will depend on the molecular weight of the counterion as well as on the particular application, but suitably may be present in an effective but non-toxic amount, usually within the range of 0.1 to 2% by weight. In some embodiments, a fluoride source selected from sodium fluoride, stannous fluoride, sodium monofluorophosphate and mixtures thereof, is used, for example the toothpaste of the invention may comprise an effective amount of sodium monofluorophosphate. In some embodiments, the fluoride source is sodium monofluorophosphate in an amount of from 0.5% to 1.0% by weight; or 0.6% to 0.9%, for example 0.7% to 0.8%.

The toothpastes of any of the preceding embodiments further include humectant, i.e. one or more humectants. Examples of suitable humectants include polyhydric alcohols (polyols) such as propylene glycol, glycerin, sorbitol, xylitol or low molecular weight polyethyleneglycols (PEGs). In various embodiments, humectants can prevent hardening of paste or gel compositions upon exposure to air, and also function as sweeteners. In some embodiments, the humectant system consists primarily or solely of sorbitol, e.g., in an amount of from 16% to 26%; or from 18% to 24%; or about 21% by weight of the toothpaste composition. However, the presence of other humectants still providing satisfactory toothpaste properties is also contemplated.

The toothpastes of any of the preceding embodiments can further include one or more detergents or surfactants. Surfactants useful for the present invention include, without limitation: anionic, nonionic, and amphoteric surfactants. Surfactants may be used, for example, to provide enhanced stability of the formulation, to help in cleaning the oral cavity surfaces through detergency, and to increase foaming of the composition upon agitation, e.g., during brushing. Suitable anionic surfactants include, for example, water-soluble salts of $C_{8-20}$ alkyl sulfates, sulfonatedmonoglycerides of $C_{8-20}$ fatty acids, sarcosinates and taurates; for example sodium lauryl sulfate, sodium coconut monoglyceridesulfonate, sodium lauryl sarcosinate, sodium lauryl isoethionate, sodium laureth carboxylate and sodium dodecyl benzenesulfonate, and mixtures thereof. Suitable nonionic surfactants include, for example, poloxamers, polyoxyethylenesorbitan esters, fatty alcohol ethoxylates, alkylphenolethoxylates, tertiary amine oxides, tertiary phosphine oxides, dialkylsulfoxides, and mixtures thereof. In one embodiment, the toothpaste comprises sodium lauryl sulfate, for example in an amount of from 1% to 3%, or about 2%. The toothpaste may also or alternatively contain one or more nonpolar surfactants, for example polymers and copolymers of ethylene glycol and propylene glycol, e.g., poloxamers, i.e., nonionic triblock copolymers composed of a central hydrophobic chain of polyoxypropylene (poly(propylene oxide)) flanked by two hydrophilic chains of polyoxyethylene (poly(ethylene oxide)). The approximate lengths of the two PEG blocks is, in some embodiments, an average of about 50-150 repeat units, e.g., about 100 repeat units while the approximate length of the propylene gycol block is an average of about 25-75 repeat unties, e.g., about 50-60 repeat units. In one embodiment, the poloxamer is poloxamer 407, also known by the BASF trade name Pluronic F127, e.g., in an amount of from 0.5% to 2%, for example about 1%. For example, in certain embodiments, the toothpastes for use in treating gingivitis may contain both sodium lauryl sulfate and a poloxamer such as poloxamer 407.

In some embodiments, the toothpastes of any of the preceding embodiments further include one or more binding and/or thickening agents. Binding agents may include polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts; and include synthetic anionic polymeric polycarboxylates, such as 1:4 to 4:1 copolymers of maleic anhydride or acid with another polymerizableethylenically unsaturated monomer, preferably methyl vinyl ether/maleic anhydride having a molecular weight (M.W.) of about 30,000 to about 1,000,000, most preferably about 300,000 to about 800,000. In some embodiments, the binding agent is derived from cellulose. In some embodiments, the binding agent includes or consists of cellulose ether, for example carboxymethylcellulose, for example CMC 2000s, in an amount of from 0.5% to 1.2%; or from 0.7% to 1.0%; or 0.8% to 0.9%.

In some embodiments, the toothpastes of any of the preceding embodiments further include one or more thickeners (i.e., thickening agents), which aid in obtaining the proper viscosity of the composition. Generally, the thickener is present in the composition in an amount of from 1% to 5%. Examples of thickening agents include, without limitation, the binding agents described above, which also modify viscosity, for example carboxyvinyl polymers, carrageenans (also known as Irish moss and more particularly iota-carrageenan), cellulosic polymers such as hydroxyethylcellulose, carboxymethylcellulose (carmellose) and salts thereof (e.g., carmellose sodium), natural gums such as karaya, xanthan, gum arabic and tragacanth, colloidal magnesium aluminum silicate, colloidal silica, and mixtures thereof. One thickener is thickener silica, for example in an amount of from 1% to 3%.

As will be evident to one of skill in the art, some components of the invention may perform multiple functions, and the identification of a compound as having one function herein is not meant to exclude its use for other functions in a particular composition. For example, a compound such as carboxymethylcellulose may act as a binder, but also has humectant and thickening properties, or a compound such as a poloxamer, while identified above as a nonionic surfactant, also has humectant and thickening properties.

It is also understood that compounds in formulation may naturally react, disassociate, and/or form complexes with one another. Accordingly, certain ingredients may be formed in situ (for example, it is understood that sodium chloride may be formed by reacting sodium hydroxide with hydrochloric acid), and also may in formulation exist in different forms (for example, to the extent the sodium chloride is dissolved, it will naturally disassociate into separate sodium and chloride ions, as opposed to a solid salt). As is usual in the art, the compositions of the invention are described in terms of exemplary formulation ingredients, without intending to exclude combinations of other ingredients that result in the same final compositions, or to exclude the natural reaction products of the described ingredient combinations.

In some embodiments, the toothpaste of any of the preceding embodiments includes from 5% to 15% sodium chloride, for example from 8% to 12% sodium chloride; from 30% to 35% calcium carbonate; from 16% to 26% sorbitol; from 1% to 3% SLS, and from 0.5% to 2% poloxamer 407. In some such embodiments, the toothpaste further includes from 0.5% to 1.0% MFP; and from 0.5% to 1.2% CMC 2000s. In some further such embodiments, the toothpaste further includes thickener silica, for example in an amount of from 1% to 3%.

In one embodiment, the toothpaste of any of the preceding embodiments includes about 32% calcium carbonate, about 21% sorbitol, about 10% sodium chloride, about 2% thickener silica, about 2% SLS, about 1.0% poloxamer 407, 0.8% to 0.9% CMC 2000s, and 0.7% to 0.8% MFP.

In some embodiments described above, the toothpastes of any of the preceding embodiments can further include one or more sweetening agents, flavoring agents and coloring agents. Any suitable flavoring or sweetening material may be employed. Examples of suitable flavoring constituents include flavoring oils, e.g. oil of spearmint, peppermint, wintergreen, clove, sage, eucalyptus, marjoram, cinnamon, lemon, and orange, and methyl salicylate. Suitable sweetening agents include sucrose, lactose, maltose, xylitol, sodium cyclamate, perillartine, AMP (aspartyl phenyl alanine methyl ester), saccharine and the like. Suitably, flavor and sweetening agents may each or together comprise from about 0.1% to 5% more of the oral care composition. In some embodiments, the toothpastes of any of the preceding embodiments include one or more flavoring agents in an amount of from about 0.5% to about 3.0%; about 0.8% to about 1.6%; or about 1.2%.

Various other materials may be incorporated in the oral preparations of this invention such as whitening agents, including urea peroxide, calcium peroxide, titanium dioxide, hydrogen peroxide, complexes of polyvinylpyrolidone (PVP) and hydrogen peroxide, preservatives, vitamins such as vitamin B6, B12, E and K, silicones, chlorophyll compounds, potassium salts for the treatment of dental hypersensitivity such as potassium nitrate as well as antitartar agents such as sodium tripolyphosphate and di- and tetra-alkali metal pyrophosphate salts such as di- and tetrasodium pyrophosphate. These agents, when present, are incorporated in the compositions of the present invention in amounts which do not substantially adversely affect the properties and characteristics desired.

In general, each of the foregoing adjuvants may be typically incorporated in the instant toothpastes in amounts up to 5% provided they do not adversely affect the stability and cleaning properties of the non-bleeding striped dentifrice of present invention.

The invention thus provides, in one embodiment, a toothpaste, e.g., a toothpaste for use in treating and/or preventing diseases or conditions of the oral cavity, e.g. gingivitis or halitosis, in a patient in need thereof, the toothpaste comprising at least 5% sodium chloride; from 5% to 15% sodium chloride; from 8% to 12% sodium chloride; or about 10% sodium chloride (Composition 1), in a toothpaste base comprising calcium carbonate abrasive and humectant, for example 1.1. Composition 1, wherein the abrasive comprises natural calcium carbonate, in an amount of from 10% to 45%; 25% to 40%; 30% to 35%; or about 32%.

1.2. Composition 1 or 1.1, further comprising a zinc salt, e.g. zinc citrate, in an amount from 0.1 to 1%; 0.1 to 0.5%; or about 0.2%.

1.3. Any foregoing composition wherein the humectant comprises a polyol, e.g., sorbitol, e.g., sorbitol in an amount of from 16% to 26%, or from 18% to 24%; or about 21%.

1.4. Any foregoing composition further comprising one or more anionic detergents or surfactants, e.g., sodium lauryl sulfate, in an amount of from 1% to 3%, or about 2%; and one or more nonionic surfactants, e.g., a poloxamer, e.g., poloxamer 407, in an amount of from 0.5% to 2%; or about 1%.

1.5. Any foregoing composition wherein the binder comprises a cellulose derivative, e.g., carboxymethylcellulose (CMC), e.g. having a medium to high degree of polymerization, e.g. 1000 to 3000, for example about 2000, e.g., in sodium salt form, e.g., CMC 2000s, in an amount effective to provide the desired viscosity, e.g., from 0.5% to 1.2%; from 0.7% to 1.0%; or 0.8% to 0.9%.

1.6. Any foregoing composition further comprising an effective amount of a fluoride ion source; e.g., sodium monofluorophosphate (MFP), in an amount of from 0.5% to 1.0%; or 0.7% to 0.8%, e.g., about 0.76%.

1.7. Any foregoing composition comprising:
from 30% to 35% calcium carbonate;
from 16% to 26% sorbitol;
from 1% to 3% sodium lauryl sulfate;
from 0.5% to 2% poloxamer 407;
from 0.5% to 1.0% sodium monofluorophosphate;
from 0.5% to 1.2% CMC; and
thickener silica in an amount of from 1% to 3%; or about 2%.

1.8. The toothpaste of any preceding composition, further comprising one or more adjuvants selected from sweetening agents flavoring agents and coloring agents, e.g., comprising a flavoring agent in an amount of from 0.5% to 3.0%; 0.8% to 1.6%; or about 1.2%.

1.9. Any foregoing composition comprising about 32% calcium carbonate, about 21% sorbitol, about 10% sodium chloride, about 2% thickener silica, about 2% SLS, about 1.0% poloxamer 407, 0.8% to 0.9% CMC, and 0.7% to 0.8% MFP.

The invention further provides, in another embodiment, a method (Method 1) for in treating and/or preventing diseases or conditions of the oral cavity, for example, treating gingivitis or halitosis, in a patient in need thereof, comprising applying a toothpaste to the gums of the patient, wherein the toothpaste is a toothpaste according to any one of Compositions 1 or 1.1-1.9. For example, wherein the toothpaste comprises at least 5% sodium chloride; from 5% to 15% sodium chloride; from 8% to 12% sodium chloride; or about 10% sodium chloride, in a toothpaste base comprising calcium carbonate abrasive and humectant. For example the invention provides:

1.1. Method 1, wherein the abrasive comprises natural calcium carbonate, in an amount of from 10% to 45%; 25% to 40%; 30% to 35%; or about 32%.

1.2. Method 1 or 1.1, wherein the toothpaste further comprises a zinc salt, e.g. zinc citrate, in an amount from 0.1 to 1%; 0.1 to 0.5%; or about 0.2%.

1.3. Any foregoing method wherein the humectant comprises a polyol, e.g., sorbitol, e.g., sorbitol in an amount of from 16% to 26%, or from 18% to 24%; or about 21%.

1.4. Any foregoing method wherein the toothpaste further comprises one or more anionic detergents or surfactants, e.g., sodium lauryl sulfate, in an amount of from 1% to 3%, or about 2%; and one or more nonionic surfactants, e.g., a poloxamer, e.g., poloxamer407, in an amount of from 0.5% to 2%; or about 1%.

1.5. Any foregoing method wherein the binder comprises a cellulose derivative, e.g., carboxymethylcellulose (CMC), e.g. having a medium to high degree of polymerization, e.g. 1000 to 3000, for example about 2000, e.g., in sodium salt form, e.g., CMC 2000s, in an amount effective to provide the desired viscosity, e.g., from 0.5% to 1.2%; from 0.7% to 1.0%; or 0.8% to 0.9%.

1.6. Any foregoing method wherein the toothpaste further comprises an effective amount of a fluoride ion source; e.g., sodium monofluorophosphate (MFP), in an amount of from 0.5% to 1.0%; or 0.7% to 0.8%, e.g., about 0.76%.

1.7. Any foregoing method wherein the toothpaste comprises:
from 30% to 35% calcium carbonate;
from 16% to 26% sorbitol;
from 1% to 3% sodium lauryl sulfate;
from 0.5% to 2% poloxamer 407;
from 0.5% to 1.0% sodium monofluorophosphate;
from 0.5% to 1.2% CMC; and
thickener silica in an amount of from 1% to 3%; or about 2%.

1.8. Any preceding method, wherein the toothpaste further comprises one or more adjuvants selected from sweetening agents flavoring agents and coloring agents, e.g., comprising a flavoring agent in an amount of from 0.5% to 3.0%; 0.8% to 1.6%; or about 1.2%.

1.9. Any foregoing method wherein the toothpaste comprises about 32% calcium carbonate, about 21% sorbitol, about 10% sodium chloride, about 2% thickener silica, about 2% SLS, about 1.0% poloxamer 407, 0.8% to 0.9% CMC, and 0.7% to 0.8% MFP.

1.10. Any foregoing method wherein the toothpaste is applied at least daily, e.g., once, twice or thrice daily, until an effect is seen, e.g., over a period of at least a week, e.g., at least two weeks, e.g., at least a month.

1.11. Any foregoing method wherein the disease or condition of the oral cavity is gingivitis or halitosis.

The invention further provides, in another embodiment, the use of sodium chloride in the manufacture of a toothpaste for treating gingivitis in a patient in need thereof, e.g., a toothpaste according to any of Compositions 1, et seq., in a method according to any of Methods 1, et seq.

The following examples are further illustrative of the nature of the present invention, but it is understood that the invention is not limited thereto. All amounts and proportions referred to herein and in the appended claims are by weight, unless otherwise indicated.

Example 1—Micro Robustness Test

The micro robustness test (MRT) is a quantitative measure of a composition's ability to withstand microbial challenge. Thus, the result is an assessment of the antimicrobial efficacy of a composition against a pool of microorganisms.

The following eleven microorganisms are included in a microorganism pool: *Burkholderiacepacia*, *Enterobacter cloacae*, *Escherichia coli*, *Klesiellaoxytoca*, *Klebsiellapneumoniae*, *Serratiamarcescens*, *Providenciarettgeri*, *Pseudomonas aeruginosa*, *Pseudomonas putida*, *Staphylococcus aureus*, and *Staphylococcus saprophyticus*.

The total microorganism's solution level is $10^7$cfu/ml. Samples are challenged three times at 60 minute intervals with $10^7$ bacteria from the microorganisms pool described above. After 4, 6 and 24 hours, aliquots are tested to measure the log reduction of bacterial level. Table 1 below shows the results for the antimicrobial test on a toothpaste of the invention having the following composition:

| | |
|---|---|
| Calcium Carbonate | 32% |
| Water | 27.9347% |
| Sorbitol | 21% |
| NaCl | 10% |
| Thickener silica | 2% |
| SLS | 2% |
| Flavor | 1.2% |
| Poloxamer 407 | 1.0% |
| CMC 2000s | 0.85% |
| MFP | 0.76% |
| and minor ingredients. | |

TABLE 1

Results for Antimicrobial Test

| Initial added bacteria level | 4 hours inoculum | 6 hours inoculum | 24 hours inoculum |
|---|---|---|---|
| $6.4 \times 10^7$ cfu/ml | <10 cfu/ml | NG (no growth) | NG (no growth) |

Table 1 shows that the bacteria tested is shown to be effectively decreased to less than <10 cfu/ml from the initiallevel of $6.4 \times 10^7$cfu/ml in 4 hours, with no growth in 6 hours or 24 hours inoculum. Thus, the high salt level toothpaste of the invention has antibacterial ability and can inhibit the growth of varieties bacteria in the toothpaste.

Example 2—Biofilm Reduction Test

Methods: Dental plaque is collected from 4 healthy volunteers and pooled together as inoculum. The O.D of the inoculum is matched to 0.3 absorbance at 610 nm. Sterile HAP disks are incubated under anaerobic conditions at 37° C. for 24 hours with 1 ml of sterile artificial saliva (with 0.01% sucrose) and 1 ml of pooled saliva in a 24 well micro plate. Freshly prepared treatment solution (1 part toothpaste of Example 1 above to 2 parts sterile distilled water) is added to the well and allowed to contact with the HAP disk for 10 minutes.

The liquid phase is removed and replaced by 2 ml of sterile artificial saliva. The disks are treated in triplicate for each control and test dentifrice for 8 days. At intervals of 2, 4 and 8 days the discs are collected aseptically and transferred into half strength pre-reduced thioglycolate medium. 100 ml of the dilution 10-4, 10-5 and 10-6 are plated in duplicates for each disk on Neomycin Vancomycin (NV) Agar, for Total Gram negative Anaerobes. Plates are surface spread using a sterile spreader and incubated anaerobically at 37° C. for 72 hours before counting the colonies. The pH is monitored for the entire period of the study using the liquid phase. The compositions of the samples used in the test are shown in Tables 2a and 2b below. Samples 1-5 contain the same formula backbone with silica base and 1.0% ZnO and 0.5% Zinc Citrate in place of sodium chloride. These samples also contain different levels essential oils:

Sample 1: Silica base formula with 1.0% ZnO and 0.5% Zinc Citrate with full essential oil cocktail level.

Sample 2: Silica base formula with 1.0% ZnO and 0.5% Zinc Citrate with half essential oil cocktail level.

Sample 3: Silica base formula with 1.0% ZnO and 0.5% Zinc Citrate with full essential oil cocktail level but half level of Thymol.

Sample 4: Silica base formula with 1.0% ZnO and 0.5% Zinc Citrate with full essential oil but half level of Thymol and *Eucalyptus*.

Sample 5: Silica base formula with 1.0% ZnO and 0.5% Zinc Citrate, no essential oil.

Sample 6: Placebo, Silica base formula without ZnO, Zinc Citrate and essential oil.

Sample 7: NCC base formula with 10% NaCl (formulation of Example 1)

Sample 8: Commercial product with 0.58% Zinc Citrate

TABLE 2a

Compositions of Samples for Biofilm Reduction Test

| | Sample | | | |
|---|---|---|---|---|
| RAW MATERIAL | 1 % | 2 % | 3 % | 4 % |
| CP water | 13.53 | 19.09 | 18.65 | 18.99 |
| sorbitol - 70% solution | 55.00 | 50.00 | 50.00 | 50.00 |
| Polyethylene Glycol 600 | 2.00 | | | |
| Glycerine | | 2.00 | 2.00 | 2.00 |
| sodium saccharin | 0.30 | 0.30 | 0.30 | 0.30 |
| ZnO | 1.00 | 1.00 | 1.00 | 1.00 |
| Zinc Citrate | 0.50 | 0.50 | 0.50 | 0.50 |
| TSPP | 0.50 | 0.50 | 0.50 | 0.50 |
| CMC - Type 12 (2000S) | 0.80 | 0.80 | 0.80 | 0.80 |
| Xanthan | 0.30 | 0.30 | 0.30 | 0.30 |
| MFP | 1.10 | 1.10 | 1.10 | 1.10 |
| Silica abrasive Zeo 114 | 10.00 | 10.00 | 10.00 | 10.00 |
| AC 43 | 5.00 | 5.00 | 5.00 | 5.00 |
| Silica thickener DT 267 | 4.00 | 4.00 | 4.00 | 4.00 |
| SLS powder | 2.00 | 2.00 | 2.00 | 2.00 |
| Betaine | 1.25 | 1.25 | 1.25 | 1.25 |
| Clove Oil | 0.177 | 0.0885 | 0.177 | 0.177 |
| Thymol | 0.25 | 0.125 | 0.125 | 0.125 |
| Eucalyptus Oil | 0.68 | 0.34 | 0.68 | 0.34 |
| Lemon Oil | 0.01 | 0.005 | 0.01 | 0.01 |
| Basil Oil (Firmenich) | 0.005 | 0.0025 | 0.005 | 0.005 |
| Maxfresh Cool Mint flavor | 1.10 | 1.10 | 1.10 | 1.10 |
| TiO2 | 0.50 | 0.50 | 0.50 | 0.50 |
| CMC - Type 8 | | | | |
| poloxomer 407 USP | | | | |
| Refined Soda | | | | |
| Natural Calcium Carbonate | | | | |
| Mint Flavor for Herbal Salt | | | | |
| Sodium Chloride | | | | |
| Sorbosil BFG51-Blue | | | | |
| Tocopheryl Acetate | | | | |

TABLE 2a-continued

Compositions of Samples for Biofilm Reduction Test

| RAW MATERIAL | Sample 1 % | Sample 2 % | Sample 3 % | Sample 4 % |
|---|---|---|---|---|
| Sodium Ascorbyl Phosphate | | | | |
| Sodium Bicarbonate | | | | |
| CI Food Blue 5 | | | | |
| TOTAL | 100.00 | 100.00 | 100.00 | 100.00 |

TABLE 2b

Compositions of Samples for Biofilm Reduction Test (cont.)

| RAW MATERIAL | Sample 5 % | Sample 6 % | Sample 7 % | Sample 8 % |
|---|---|---|---|---|
| CP water | 19.65 | 21.15 | 27.9347 | |
| sorbitol - 70% solution | 50.00 | 50.00 | 21.00 | 37.00 |
| Polyethylene Glycol 600 | | | | |
| Glycerine | 2.00 | 2.00 | | |
| sodium saccharin | 0.30 | 0.30 | 0.30 | |
| ZnO | 1.00 | | | |
| Zinc Citrate | 0.50 | | | 0.58 |
| TSPP | 0.50 | 0.50 | | |
| CMC - Type 12 (2000S) | 0.80 | 0.80 | | |
| Xanthan | 0.30 | 0.30 | 0.20 | |
| MFP | 1.10 | 1.10 | 0.76 | |
| Silica abrasive Zeo 114 | 10.00 | 10.00 | | 15.00 |
| AC 43 | 5.00 | 5.00 | | |
| Silica thickener DT 267 | 4.00 | 4.00 | 2.00 | |
| SLS powder | 2.00 | 2.00 | 2.00 | 2.00 |
| Betaine | 1.25 | 1.25 | | |
| Clove Oil | | | | Commercial Product |
| Thymol | | | | |
| Eucalyptus Oil | | | | |
| Lemon Oil | | | | |
| Basil Oil (Firmenich) | | | | |
| Maxfresh Cool Mint flavor | 1.10 | 1.10 | | |
| TiO2 | 0.50 | 0.50 | | |
| CMC - Type 8 | | | 0.85 | |
| poloxomer 407 USP | | | 1.00 | |
| Refined Soda | | | 0.40 | |
| Natural Calcium Carbonate | | | 32.00 | |
| Mint Flavor for Herbal Salt | | | 1.20 | |
| Sodium Chloride | | | 10.00 | |
| Sorbosil BFG51-Blue | | | 0.20 | |
| Tocopheryl Acetate | | | 0.05 | |
| Sodium Ascorbyl Phosphate | | | 0.01 | |
| Sodium Bicarbonate | | | 0.10 | |
| CI Food Blue 5 | | | 0.00 | |
| TOTAL | 100.00 | 100.00 | 100.00 | |

TABLE 3

Results of Biofilm Reduction Test

| Sample | Total Gram Negative Anaerobes on NV Agar, Log CFU/ml |
|---|---|
| Sample 1: Silica base with 1.0% ZnO and 0.5% Zinc Citrate with full essential oil cocktail level | 4.59 |
| Sample 2: Silica base with 1.0% ZnO and 0.5% Zinc Citrate with half essential oil cocktail level | 4.74 |
| Sample 3: Silica base with 1.0% ZnO and 0.5% Zinc Citrate with full essential oil cocktail level but half level of Thymol | 4.79 |
| Sample 4: Silica base with 1.0% ZnO and 0.5% Zinc Citrate with full essential oil but half level of Thymol and Eucalyptus | 4.82 |
| Sample 5: Silica base with 1.0% ZnO and 0.5% Zinc Citrate, no essential oil | 4.86 |
| Sample 6: Placebo, Silica base formula without ZnO, Zinc Citrate and essential oil | 6.09 |
| Sample 7: NCC base formula with 10% NaCl | 4.47 |
| Sample 8: Commercial product with 0.58% Zinc Citrate | 5.02 |

It can be seen from the data in Table 3 that the efficacy of the actives are found to be in the following order (from the most efficacious to less):

a. Sample 7: NCC base formula with 10% NaCl
b. Sample 1: Silica base formula with 1.0% ZnO and 0.5% Zinc Citrate with full essential oil cocktail level
c. Sample 2: Silica base formula with 1.0% ZnO and 0.5% Zinc Citrate with half essential oil cocktail level
d. Sample 3: Silica base formula with 1.0% ZnO and 0.5% Zinc Citrate with full essential oil cocktail level but half level of Thymol
e. Sample 4: Silica base formula with 1.0% ZnO and 0.5% Zinc Citrate with full essential oil but half level of Thymol and *Eucalyptus*.
f. Sample 5: Silica base formula with 1.0% ZnO and 0.5% Zinc Citrate, no essential oil
g. Sample 8: Commercial product with 0.58% Zinc Citrate
h. Sample 6: Placebo, Silica base formula without ZnO, Zinc Citrate and essential oil The results indicate that the toothpaste having 10% sodium chloride in combination with a natural calcium carbonate base, as opposed to a silica abrasive base, has better efficacy on biofilm reduction than a variety of silica-based toothpastes comprising a variety of antibacterial agents. This reduction in biofilm corresponds to a reduction in the amount of dental plaque when the toothpaste is used regularly, thereby providing a reduction in the incidence and severity of gingivitis.

Example 3—In Vitro Antibacterial Efficacy Study

Methods: Four sample toothpaste compositions are selected for the study

Sample 1: NCC base with 10% Sodium Chloride and 0.2% Zn Citrate
Sample 2: NCC base with 10% Sodium Chloride
Sample 3: Silica base with 10% Sodium Chloride and 0.2% Zn Citrate Sample 4: Silica base with 10% Sodium Chloride The samples are tested at 5-fold serial dilutions in sterile water. 4.5 mL of the sample is used for each time interval. The inoculum is prepared in the selected medium and adjusted to 0.5 McFarland standard (*Actinomycetes viscous* ATCC 43146, *Streptococcus oralis* ATCC 35037, *Veillonellaparvula* ATCC 17745, *Lactobacillus casei* ATCC 334, and *Fusobacteriumnucleatum* ATCC 10953). Each sample and the control are inoculated with 0.5 mL of the prepared medium. At the end of the selected contact time, 0.5 mL of the inoculated sample is pipetted into 4.5 mL of D/E neutralizing broth. The mixture is vortexed thoroughly. 1:10 dilutions of each sample are prepared using D/E broth. 100 μL of each dilution is pipetted onto sterile Blood agar plates and spread over the entire surface using a sterile spreader. The plates are inverted and incubated at 37° C. under anaerobic conditions for 48-72 hours. For each plate, the number of colonies are counted to determine the cfu count for all dilutions, and thereby the average cfu/mL for each dilution. The percent reduction is then calculated as; control cfu count−average cfu count/control cfu count×100. Log reduction values are also calculated.

Results: The following table summarized the results obtained:

| | Bacteria Reduction, % (2 mins) | | | | | | | | |
|---|---|---|---|---|---|---|---|---|---|
| Sample | *A. viscous* | | *S. oralis* | | *L. casei* | | *V. parvula* | | *F. nucleatum* | |
| 1 | 50.49 | +33% | 49.90 | +35% | 52.08 | +30% | 57.68 | +13% | 58.08 | +15% |
| 2 | 37.96 | | 37.03 | | 39.98 | | 51.08 | | 50.35 | |
| 3 | 41.00 | +4% | 49.42 | −4% | 40.08 | −4% | 44.47 | +2% | 50.59 | −2% |
| 4 | 39.33 | | 40.92 | | 41.57 | | 43.53 | | 51.76 | |

From the results obtained above, it is clear that the addition of 0.2% zinc citrate to an NCC/sodium chloride toothpaste increases the bacterial reduction efficacy by about 13% to 35%, depending on the bacterial strain (compare sample 1 to sample 2). In contrast, the addition of 0.2% zinc citrate to a silica/sodium chloride toothpaste has no significant effect (compare sample 3 to sample 4). There is neither a consistent increase nor decrease in bacterial reduction efficacy. In addition, comparing sample 1 to sample 3, it is apparent that, in the presence of zinc citrate, NCC based toothpaste is significantly more effective in bacterial reduction than silica based toothpaste for four of the five strains studied (e.g., for *A. viscous,* 50.49% reduction with NCC, but only 41.00% reduction with silica). In contrast, comparing sample 2 to sample 4, it is apparent that in the absence of zinc citrate, NCC based toothpaste is comparable in bacterial reduction efficacy to silica based toothpaste for four out of the five strains studied (e.g., for *A. viscous,* 37.96% reduction with NCC and 39.33% reduction for silica).

While the present invention has been described with reference to embodiments, it will be understood by those skilled in the art that various modifications and variations may be made therein without departing from the scope of the present invention as defined by the appended claims.

What is claimed is:

1. A toothpaste composition comprising (a) 10% to 45% natural calcium carbonate, (b) 8% to 12% sodium chloride, and (c) an effective antimicrobial amount of a zinc salt, in an amount of 0.1 to 1%, all percentages by weight of the composition.

2. The composition of claim 1, wherein the natural calcium carbonate is present in an amount of from 25% to 40% by weight of the composition.

3. The composition of claim 1 wherein the toothpaste comprises about 10% sodium chloride by weight of the composition.

4. The composition of claim 1 wherein the zinc salt comprises 0.1 to 0.5% by weight of the composition.

5. The composition of claim 1 wherein the zinc salt is zinc citrate.

6. The composition of claim 1 further comprising a humectant.

7. The composition of claim 6, wherein the humectant comprises one or more polyols in an amount of from 16% to 26% by weight of the composition.

8. The composition of claim 1 wherein the toothpaste further comprises one or more detergents or surfactants in an amount of from 1% to 3%; and a poloxamer in an amount of from 0.5% to 2% by weight of the composition.

9. The composition of claim 1 wherein the toothpaste further comprises one or more binding agents, in an amount of from 0.5% to 1.2% by weight of the composition.

10. The composition of claim 1 wherein the toothpaste further comprises a fluoride source, in an amount of from 0.5% to 1.0% by weight of the composition.

11. The composition of claim 1 wherein the toothpaste further comprises thickener silica in an amount of from 1% to 3%.

12. The composition of claim 1 wherein the toothpaste further comprises one or more adjuvants selected from sweetening agents, flavoring agents and coloring agents.

13. The composition of claim 1 wherein the toothpaste further comprises a flavoring agent in an amount of from 0.5% to 3.0%.

14. A method of treating and/or preventing a disease or condition of the oral cavity, in a patient in need thereof, comprising applying a toothpaste to the gums of the patient, wherein the toothpaste is a composition according to claim 1.

15. The method of claim 14, wherein the disease or condition of the oral cavity is halitosis or gingivitis.

* * * * *